(12) United States Patent
Heinrich et al.

(10) Patent No.: US 7,829,565 B2
(45) Date of Patent: Nov. 9, 2010

(54) INDOLE DERIVATIVES AS SEROTONIN REUPTAKE INHIBITORS

(75) Inventors: Timo Heinrich, Groβ-Umstadt (DE); Henning Böttcher, Darmstadt (DE); Kai Schiemann, Seeheim-Jugenheim (DE); Günter Hölzemann, Seeheim-Jugenheim (DE); Christoph van Amsterdam, Darmstadt (DE); Gerd Bartoszyk, Weiterstadt (DE); Joachim Leibrock, Pfungstadt (DE); Christoph Seyfried, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 249 days.

(21) Appl. No.: 10/560,734

(22) PCT Filed: May 24, 2004

(86) PCT No.: PCT/EP2004/005547
§ 371 (c)(1),
(2), (4) Date: Dec. 15, 2005

(87) PCT Pub. No.: WO2004/113326
PCT Pub. Date: Dec. 29, 2004

(65) Prior Publication Data
US 2007/0099933 A1 May 3, 2007

(30) Foreign Application Priority Data
Jun. 16, 2003 (DE) .................. 10326939

(51) Int. Cl.
*A61K 31/497* (2006.01)
*A61K 31/445* (2006.01)
*C07D 295/00* (2006.01)
*C07D 241/04* (2006.01)
*C07D 211/00* (2006.01)
*A01N 43/40* (2006.01)

(52) U.S. Cl. .................. 514/252.12; 544/358
(58) Field of Classification Search ........................ None
See application file for complete search history.

(56) References Cited

U.S. PATENT DOCUMENTS

| | | | |
|---|---|---|---|
| 2004/0147528 A1* | 7/2004 | Bathe et al. ............ | 514/254.09 |
| 2006/0122191 A1* | 6/2006 | Heinrich et al. ........ | 514/254.03 |
| 2006/0160824 A1* | 7/2006 | Heinrich et al. ........ | 514/254.09 |

FOREIGN PATENT DOCUMENTS

| | | | |
|---|---|---|---|
| DE | 10353657 | * | 6/2005 |
| WO | WO 02/39989 | * | 5/2002 |
| WO | WO 02/102794 | * | 12/2002 |

OTHER PUBLICATIONS

Vippagunta et al. Advanced Drug Delivery Reviews, 2001, 48, 3-26.*
Greene. Protective Groups in Organic Synthesis, 1999, pp. 17-23.*
March. Advanced Organic Chemistry, 1992, pp. 357-362.*
Farvolden et al. Expert Opinion on Investigational Drugs, 2003, 12(1), 65-86.*
Pillay et al. Expert Opinion on Investigational Drugs, 2007, 12(4), 541-54.*
Legos et al. Expert Opinion on Investigational Drugs, 2002, 11(5), 603-614.*
Waeber Expert Opinion on Investigational Drugs, 2003, 8(2), 437-56.*
Schurks. Expert Opinion on Drug Metabolism Toxicology, 2009, 5(9), 1141-48.*
Grigoriadis. Expert Opinion in Therapeutic Targets, 2009, 9(4), pp. 651-684.*
Czlonkowska et al. Expert Opinion in Pharmacotherapy, 2009, 10(8), pp. 1249-1259.*

* cited by examiner

*Primary Examiner*—James O Wilson
*Assistant Examiner*—Noble Jarrell
(74) *Attorney, Agent, or Firm*—Millen, White, Zelano, Branigan, P.C.

(57) ABSTRACT

Compounds of the formula (I), the use thereof for the preparation of a medicament for the treatment of diseases associated with the serotonin receptor and/or serotonin reuptake, in particular for the preparation of a medicament as anxiolytic, antidepressant, neuroleptic and/or antihypertonic and/or for positively influencing obsessive-compulsive disorder (OCD), sleeping disorders, tardive dyskinesia, learning disorders, age-dependent memory disorders, eating disorders, such as bulimia, and/or sexual dysfunctions. The compounds bind to the 5-$HT_{1A}$ receptor.

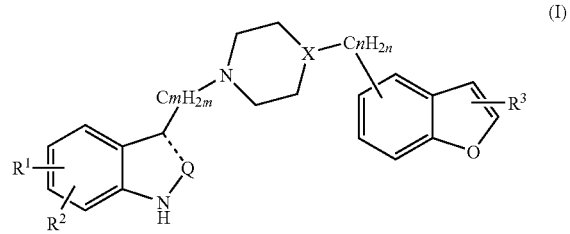

8 Claims, No Drawings

INDOLE DERIVATIVES AS SEROTONIN REUPTAKE INHIBITORS

The present invention relates to novel indole derivatives, processes for the preparation thereof and use of the compounds for the preparation of medicaments for the treatment and prophylaxis of diseases associated with serotonin reuptake and/or serotonin receptors (serotonin, 5-hydroxytryptamine, 5-HT).

The following types of 5-HT receptor are known, for example: $5\text{-}HT_{1A}$, $5\text{-}HT_{1B}$, $5\text{-}HT_{1D}$, $5\text{-}HT_{2A}$, $5\text{-}HT_{2B}$, $5\text{-}HT_{2C}$, $5\text{-}HT_3$, $5\text{-}HT_4$, $5\text{-}HT_6$, $5\text{-}HT_7$. Sub-types, such as, for example, $5\text{-}HT_{1D\alpha}$ and $5\text{-}HT_{1D\beta}$, which differ in tissue specificity, mode of action and further properties, are also found.

WO9951575 discloses indole derivatives which influence $5\text{-}HT_{1A}$ auto-receptors and 5-HT transporters and can be employed for the treatment of depression.

DE19514567 describes piperazinylbenzofurans having actions on the central nervous system, EP0655442 describes piperazine derivatives having a tachykinin-antagonistic action.

Indolepiperazine derivatives are known from EP0648767, U.S. Pat. No. 5,532,241, EP0407844, EP0376607, BE771285, GB1075156, GB118064, FR1551082 and from EP 0 736 525. These compounds are effective serotonin reuptake inhibitors and $5\text{-}HT_{1A}$ receptor agonists.

WO9616056, WO9617842, WO9718202, WO9718203, WO9745432 and WO9719943 disclose indoiepiperidine and indolepiperazine derivatives which are effective $5\text{-}HT_{1D\alpha}$ receptor agonists. The compounds disclosed therein are used for the treatment of diseases in connection with migraine owing to their vasoconstrictive action.

The invention had the object of finding novel compounds which can be used for the preparation of medicaments.

It has been found that the compounds of the formula I according to the invention and physiologically acceptable acid-addition salts thereof have valuable pharmacological properties while being well tolerated. Surprisingly, it has been found that the compounds of the formula 1 according to the invention have actions on the central nervous system. They act as selective serotonin reuptake inhibitors, exhibit serotonin-agonistic and -antagonistic properties and thus influence serotoninergic transmission. In particular, they exhibit $5\text{-}HT_{1A}$-agonistic actions.

The invention therefore relates to compounds of the formula I

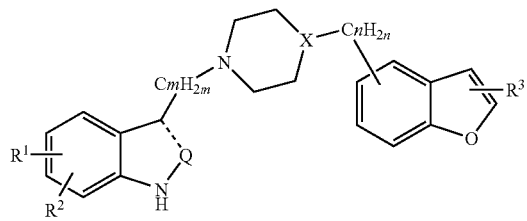

I in which
X=N or CH,
$R^1$, $R^2$, $R^3$=independently of one another OH, OA, CN, Hal, $COR^4$ or $CH_2R^4$,
$R^4$=OH, OA, $NH_2$, NHB or $NB_2$,
Q=$CH_2$, CO and, if divalent, also CH, A, B=independently of one another straight-chain or branched alkyl or alkoxy having 1 to 10 C atoms, alkenyl having 2 to 10 C atoms or alkoxyalkyl having 2 to 10 C atoms,
m=2, 3, 4, 5 or 6 and
n=0, 1, 2, 3 or 4, and physiologically acceptable salts, derivatives, solvates and stereoisomers thereof, including mixtures thereof in all ratios.

A and B, independently of one another, denote alkyl, are preferably unbranched and have 1, 2, 3, 4, 5, 6, 7, 8, 9 or 10 C atoms, preferably 1, 2, 3, 4, 5 or 6 C atoms, and preferably denotes methyl, ethyl, n-propyl, furthermore preferably isopropyl, butyl, isobutyl, sec-butyl or tert-butyl, but also n-pentyl, neopentyl, isopentyl or n-hexyl. Particular preference is given to methyl, ethyl, n-propyl, isopropyl, n-butyl, n-pentyl, n-hexyl or n-decyl.

Alkenyl preferably stands for allyl, 2- or 3-butenyl, isobutenyl, sec-butenyl, preference is furthermore given to 4-pentenyl, isopentenyl or 5-hexenyl.

Alkoxy denotes $-O(CH_2)_m CH_3$, in which m denotes 1, 2, 3, 4, 5, 6, 7, 8 or 9, but in particular 2. Alkoxyalkyl denotes $-(CH_2)_n O(CH_2)_m CH_3$, for example methoxymethylene or propoxypropylene, where m or n, independently of one another, can be 1, 2, 3, 4, 5 or 6.

Hal preferably denotes F, Cl or Br, but also I.

The compounds of the formula I according to the invention encompass the compounds of the formula Ia and Ib, in which X, $R^1$, $R^2$, $R^3$, Q, m and n have the above meanings

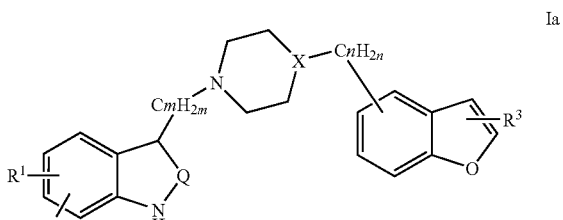

Ia

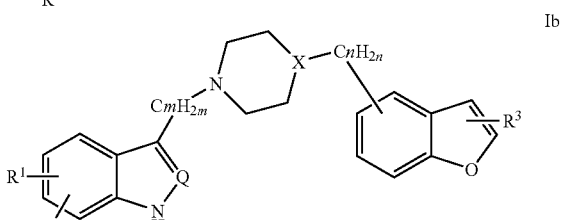

Ib

Preference is given to compounds of the formula I in which
X=N,
$R^1$, $R^2$, $R^3$=independently of one another CN, OH, $COR^4$ or $CH_2R^4$,
$R^4$=OH, $NH_2$, NHB or $NHB_2$,
Q=$CH_2$, CO and, if divalent, also CH,
B=alkyl having 1-6 C atoms,
m=4 and
n=0, and physiologically acceptable salts, derivatives, solvates and stereoisomers thereof, including mixtures thereof in all ratios.

Particular preference is given to the compounds 5-{4-[4-(5-cyano-2,3-di-hydro-1H-indol-3-yl)butyl]piperazin-1-yl}benzofuran-2-carboxamide,

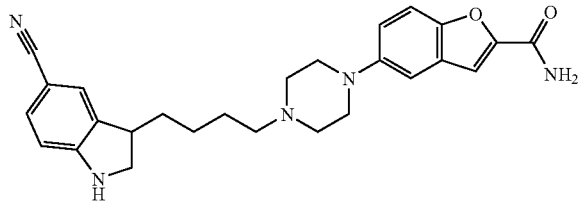

5-{4-[4-(5-cyano-6-hydroxy-1H-indol-3-yl)butyl]piperazin-1-yl}benzofuran-2-carboxamide,

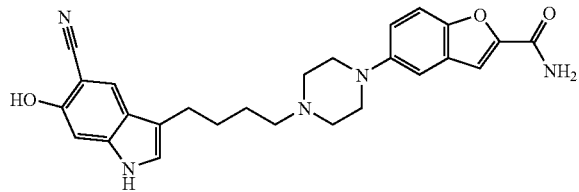

and 5-{4-[4-(5-cyano-2-oxo-2,3-dihydro-1H-indol-3-yl)butyl]piperazin-1-yl}-benzofuran-2-carboxamide.

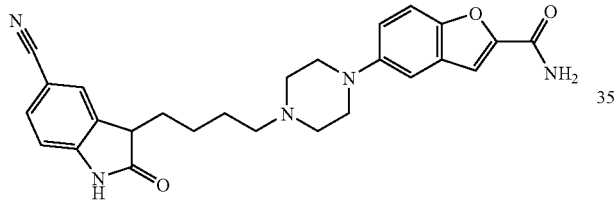

Also according to the invention are all physiologically acceptable salts, derivatives, solvates and stereoisomers of these compounds, including mixtures thereof in all ratios.

The invention also relates to the optically active forms (stereoisomers), the enantiomers, the racemates, the diastereomers and hydrates and solvates of these compounds.

Pharmaceutically or physiologically acceptable derivatives are taken to mean, for example, salts of the compounds according to the invention and also so-called prodrug compounds. Prodrug compounds are taken to mean compounds of the formula I modified by, for example, alkyl or acyl groups, sugars or oligopeptides which are rapidly cleaved or liberated in the organism to give the active compounds according to the invention. These also include biodegradable polymer derivatives of the compounds according to the invention, as described, for example, in Int. J. Pharm. 115 (1995), 61-67.

Suitable acid-addition salts are inorganic or organic salts of all physiologically or pharmacologically acceptable acids, for example halides, in particular hydrochlorides or hydrobromides, lactates, sulfates, citrates, tartrates, maleates, fumarates, oxalates, acetates, phosphates, methylsulfonates or p-toluenesulfonates.

Solvates of the compounds of the formula I are taken to mean adductions of inert solvent molecules onto the compounds of the formula I which form owing to their mutual attractive force. Solvates are, for example, hydrates, such as monohydrates or dihydrates, or alcoholates, i.e. addition compounds with alcohols, such as, for example, with methanol or ethanol.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. Particular preference is given to mixtures of two stereoisomeric compounds.

The invention additionally relates to a process for the preparation of the compounds of the formula I, characterised in a) that a compound of the formula II, in which $R^1$, $R^2$, $R^3$, X, m and n have the above-mentioned meanings

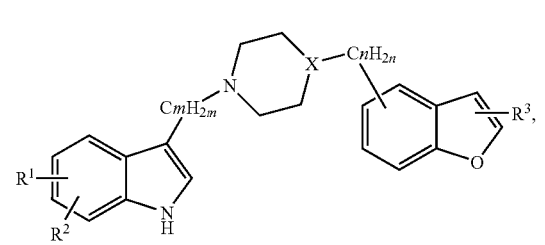

is reacted with dimethyl sulfoxide and concentrated HCl, or b) that a compound of the formula III, in which $R^1$, $R^2$, and n have the above-mentioned meanings and Y is a halogen, in particular chlorine, or an alcohol provided with protecting groups known to the person skilled in the art,

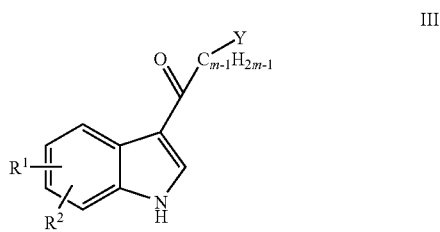

is reacted with trifluoroacetic acid and triethylsilane and is subsequently coupled with a compound of the formula IV, in which $R^3$, X and n have the above-mentioned meanings,

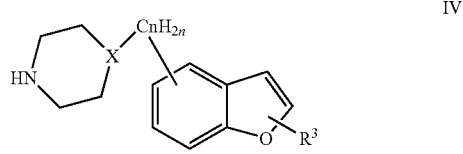

or c) that a compound of the formula V, in which $R^2$ and m have the above-mentioned meanings, and Y is a halogen, in particular chlorine, or an alcohol provided with protecting groups known to the person skilled in the art,

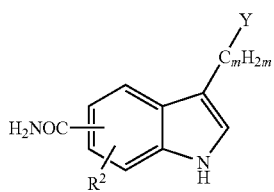

is reacted with a dehydrating reagent and is subsequently coupled with a compound of the formula IV.

It is also possible to carry out the reaction in each case stepwise.

The starting compounds of the formula II, III, VI and V are generally known. If they are novel, they can be prepared by methods known per se.

If desired, the starting materials can also be formed in situ so that they are not isolated from the reaction mixture, but instead are immediately converted further into the compounds of the formula I.

The starting materials can be combined (melted) in the absence of a solvent in a sealed reaction vessel or an autoclave. However, it is also possible to allow the starting materials to react in the presence of an inert solvent.

Suitable inert solvents are, for example, heptane, hexane, petroleum ether, benzene, toluene, xylene, trichloroethylene-, 1,2-dichloroethanetetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether (methyl glycol or ethyl glycol), ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; esters, such as ethyl acetate, carboxylic acids or acid anhydrides, such as, for example, such as, acetic acid or acetic anhydride, nitro compounds, such as nitromethane or nitrobenzene, if desired also mixtures of the said solvents with one another or mixtures with water.

The amount of solvent is not crucial, preferably 10 g to 500 g of solvent can be added per g of the compound of the formula I to be reacted.

It may be advantageous to add an acid-binding agent, for example an alkali metal or alkaline earth metal hydroxide, carbonate or bicarbonate or other alkali metal or alkaline earth metal salts of weak acids, preferably a potassium, sodium or calcium salt, or to add an organic base, such as, for example, triethylamine, dimethylamine, pyridine or quinoline, or an excess of the amine component.

Suitable reaction temperatures are at temperatures of 10 to 180° C., preferably at 20 to 150° C. and very particularly preferably at 40 to 100° C.

The reaction is preferably carried out at a pressure of 1 to 200 bar and at temperatures between −80° and +150° C., particularly preferably at 40 to 100° C. and atmospheric pressure. Preferably at 1.5 to 120 bar and in particular at 2 to 100 bar.

The duration of the reaction depends on the selected reaction conditions. In general, the reaction duration is 0.5 hours to 10 days, preferably 1 to 24 hours.

The compounds of the formula I and also the starting materials for the preparation thereof are, in addition, prepared by known methods, as described in the literature (for example in standard works, such as Houben-Weyl, Methoden der organischen Chemie [Methods of Organic Chemistry], Georg-Thieme-Verlag, Stuttgart), thus, for example, under reaction conditions which are known and suitable for the said reactions. Use can also be made here of variants known per se, which are not described here in greater detail.

The compounds of the formula II can be obtained, after removal of the solvent, by conventional work-up steps, such as, for example, addition of water to the reaction mixture and extraction. It may be advantageous subsequently to carry out a distillation or crystallisation for further purification of the product.

An acid of the formula I can be converted into the associated addition salt using a base, for example by reaction of equivalent amounts of the acid and the base in an inert solvent, such as ethanol, followed by evaporation. Particularly suitable bases for this reaction are those which give physiologically acceptable salts. Thus, the acid of the formula I can be converted into the corresponding metal salt, in particular alkali metal or alkaline earth metal salt, or into the corresponding ammonium salt using a base (for example sodium hydroxide, potassium hydroxide, sodium carbonate or potassium carbonate). Also suitable for this reaction are organic bases which give physiologically acceptable salts, such as, for example, ethanolamine.

On the other hand, a base of the formula I can be converted into the associated acid-addition salt using an acid, for example by reaction of equivalent amounts of the base and the acid in an inert solvent, such as ethanol, followed by evaporation. Particularly suitable acids for this reaction are those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic, mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxysulfonic acid, benzenesulfonic acid, p-toluenesulfonic acid, naphthalenemono- and disulfonic acids or laurylsulfuric acid. Salts with physiologically unacceptable acids, for example picrates, can be used for the isolation and/or purification of the compounds of the formula I.

It has been found that the compounds of the formula I and physiologically acceptable acid-addition salts thereof are well tolerated and have valuable pharmacological properties since they exhibit particular actions on the central nervous system. In particular, they inhibit 5-HT reuptake. In addition, the compounds have high affinity to the $5\text{-HT}_{1A}$ receptor and exhibit serotonin-agonistic and -antagonistic properties. Due to a 5-HT-agonistic action and 5-HT reuptake inhibition, serotonin remains in the synaptic cleft for longer and the serotonin action is reinforced. Active ingredients having such properties are therefore particularly suitable as antidepressants and anxiolytics. The compounds of the formula I inhibit the binding of tritiated serotonin ligands to hippocampal receptors (Cossery et al., European J. Pharmacol. 140 (1987), 143-155) and synaptosomal serotonin reuptake (Sherman et al., Life Sci. 23 (1978), 1863-1870).

For in-vitro determination of 5-HT reuptake inhibition, synaptosomal reuptake inhibition (Wong et al., Neuropsycho-pharmacology 8 (1993), 22-33) and p-chloroamphetamine antagonism (Fuller et al. J. Pharmacol. Exp. Ther. 212 (1980), 115-119) is measured. Serotonin reuptake inhibition can in addition also be investigated with the aid of the Waldmeier method ex vivo in the brain tissue of mice (European J. Pharmacol. 1977, 46, 387-92), and by microdialysis, which is described by DiChiara (Trends in Pharmacol. Sci., 11 (1990), 116-121). To this end, a physiological solution is perfused through a microdialysis container implanted into a rat brain. During this perfusion, the solution takes up the neurotransmitters liberated in the brain and is subsequently analysed. Thus, the 5-HT content in the solution after perfusion is proportional to the amount liberated in the brain and it increases, for example, after administration of a 5-HT reuptake inhibitor (Gardier et al., Fundam. Clin. Pharmacol., 10 (1996), 16-27).

The $5\text{-HT}_{1A}$-agonistic action can be measured in vitro, for example, with the aid of the (serotonin) binding test, as described by Matzen et al. (J. Med. Chem., 43 (2000), 1149-57), in particular on page 1156 with reference to Eur. J. Pharmacol., 140 (1987), 143-155. In addition, the $5\text{-HT}_{1A}$-agonistic action can be measured with the aid of the GTP-gammaS test described by Newman-Tancredi et al. (Eur. J. Pharmacol. 307 (1996), 107-11).

Furthermore, changes in DOPA accumulation in the striatum and 5-HT accumulation in the N. raphe may occur after administration of the compounds of the formula I (Seyfried et al., Europ. J. Pharmacol. 160 (1989), 31-41). In addition, analgesic and hypotensive actions may occur. Thus, in catheterised, conscious, spontaneously hypertonic rats (method cf. Weeks and Jones, Proc. Soc. Exptl. Biol. Med. 104 (1960), 646-648), the directly measured blood pressure drops after peroral administration of the compounds. Compounds of the formula I are therefore also suitable for the prophylaxis and treatment of the consequences of cerebral infarctions (apoplexia cerebri), such as strokes and cerebral ischaemia.

The invention relates, in particular, to the use of the compounds of the formula I and physiologically acceptable salts, derivatives, solvates and stereoisomers thereof, including mixtures thereof in all ratios, as serotonin receptor ligands and/or for serotonin reuptake inhibition. In particular, the use of the compounds of the formula I as $5\text{-HT}_{1A}$ agonists and as inhibitors of 5-HT reuptake is in accordance with the invention.

The invention thus also relates, in particular, to the use of compounds of the formula I and/or physiologically acceptable salts, derivatives, solvates and stereoisomers thereof, including mixtures thereof in all ratios, for the preparation of a medicament for the treatment of diseases, in particular of diseases associated with the serotonin receptor and/or serotonin reuptake.

Compounds of the formula I according to the invention may be chiral owing to their molecular structure and can accordingly occur in various enantiomeric forms. They can therefore be in racemic or in optically active form. Since the pharmaceutical efficacy of the racemates or stereoisomers of the compounds according to the invention may differ, it may be desirable to use the enantiomers. In this cases, the end product or alternatively even the intermediates can be resolved to give enantiomeric compounds, by chemical or physical measures known to the person skilled in the art, or even employed as such in the synthesis.

Since compounds of the formula I inhibit serotonin reuptake and at the same time have $5\text{-HT}_{1A}$-agonistic properties, they are particularly suitable as antidepressants and anxiolytics.

The invention therefore also relates to the use of compounds of the formula I and/or physiologically acceptable salts, derivatives, solvates, and stereoisomers thereof, including mixtures thereof in all ratios, for the preparation of a medicament as anxiolytic, antidepressant, neuroleptic and/or antihypertonic and/or for positively influencing obsessive-compulsive disorder (OCD), sleeping disorders, tardive dyskinesia, learning disorders, age-dependent memory disorders, eating disorders, such as bulimia, and/or sexual dysfunctions. The use for the preparation of a medicament as antidepressant is particularly preferred. Compounds of the formula I may furthermore and also be used as intermediates for the preparation of other medicament active ingredients.

The compounds of the formula I are suitable both in veterinary and also in human medicine for the treatment of dysfunctions of the central nervous system and of inflammation.

The invention thus relates to the use of compounds of the formula I and/or physiologically acceptable salts, derivatives, solvates and stereoisomers thereof, including mixtures thereof in all ratios, for the preparation of a medicament for the treatment of psychoses, schizophrenia, schizo-affective psychosis, cyclothymia, epilepsy, cramps, depression (subtypes of severe depression and cyclothymic depression), pathogenic anxiety states (subtypes of panic attacks with or without agoraphobia), superexcitation, hyperactivity, stress illnesses, post-traumatic stress disorders, sleeping disorders, narcolepsy, cyclic manic depression, attention disorders in children and youths, severe developmental disorders and disorders of social behaviour with mental retardation, obsessive-compulsive disorders in the narrower (OCD) and broader sense (OCSD), addiction disorders, disorders in nutrient uptake or eating disorders, for example bulimia, obesity or anorexia nervosa, fibromyalgia, and psychiatric symptoms in senile dementia and Alzheimer's-type dementia, cognitive impairments (learning and memory disorders), in particular age-dependent memory disorders, dementia, tardive dyskinesia, neurodegenerative diseases, such as Parkinson's disease, Alzheimer's disease, Huntington's disease, lathyrism, amyotrophic lateral sclerosis, Lewy bodies dementia, Tourette's syndrome, sexual dysfunctions, premenstrual syndrome, acromegaly, hypogonadism, secondary amenorrhea, undesired puerperal lactation, extrapyramidal motor disorders, for the treatment of side effects arising in the treatment of extrapyramidal motor disorders with conventional anti-Parkinson's medicaments and of extrapyramidal symptoms (EPS), tension states, side effects of hypertonia treatment induced by neuroleptics (for example with α-methyl-dopa) or for the prophylaxis, treatment and control of cerebral infarctions (apoplexia cerebri), such as strokes and cerebral ischaemia, or for the treatment of pain, in particular chronic pain, migraine, CNS trauma, hypoglycemia, asthma, glaucoma, cytomegaly and for the treatment of other degenerative retinal diseases, incontinence, tinnitus, or for the treatment of loss of hearing induced by aminoglycoside antibiotics.

In particular, however, they are suitable as medicament active ingredients for anxiolytics, antidepressants, antipsychotics, neuroleptics, antihypertonics and/or for positively influencing obsessive-compulsive disorder (OCD), sleeping disorders, tardive dyskinesia, learning disorders, age-dependent memory disorders, eating disorders, such as bulimia, and/or sexual dysfunctions.

The compounds of the formula I can be used for the preparation of pharmaceutical compositions, in particular by non-chemical methods. Here, they are brought into a suitable dosage form together with at least one solid, liquid and/or semi-liquid excipient or adjuvant and optionally in combination with one or more further active ingredient(s).

The invention therefore furthermore relates to pharmaceutical compositions comprising at least one compound of the formula I and/or physiologically acceptable salts, derivatives, solvates, and stereoisomers thereof, including mixtures thereof in all ratios. The invention also relates, in particular, to pharmaceutical compositions which comprise further excipients and/or adjuvants and also to pharmaceutical compositions which comprise at least one further medicament active ingredient.

The invention also relates, in particular, to a process for the preparation of a pharmaceutical composition, characterised in that a compound of the formula I and/or one of its physiologically acceptable salts, derivatives, solvates, and stereoisomers, including mixtures thereof in all ratios, is brought into a suitable dosage form together with a solid, liquid or semi-liquid excipient or adjuvant and optionally with a further medicament active ingredient.

The pharmaceutical compositions according to the invention can be used as medicaments in human or veterinary medicine.

Suitable excipient substances are organic or inorganic substances which are suitable for enteral (for example oral), parenteral or topical administration and do not react with the novel compounds, for example water, vegetable oils (such as sunflower oil or cod-liver oil), benzyl alcohols, polyethylene glycols, gelatine, carbohydrates, such as lactose or starch, magnesium stearate, talc, lanolin or Vaseline. On the basis of his expert knowledge, the person skilled in the art is familiar with which adjuvants are suitable for the desired medicament formulation. Besides solvents, for example water, physiological saline solution or alcohols, such as, for example, ethanol, propanol or glycerol, sugar solutions, such as glucose or mannitol solutions, or a mixture of the said solvents, gel formers, tablet assistants and other active-ingredient excipients, it is possible to use, for example, lubricants, stabilisers and/or wetting agents, emulsifiers, salts for modifying the osmotic pressure, antioxidants, dispersants, antifoams, buffer substances, flavours and/or aroma substances or flavour correctants, preservatives, solubilisers or dyes. If desired, compositions or medicaments according to the invention may comprise one or more further active ingredients, for example one or more vitamins.

The invention also relates to a set (kit) consisting of separate packs of
a) an effective amount of a compound of the formula I and/or physiologically acceptable salts, derivatives, solvates and stereoisomers thereof, including mixtures thereof in all ratios, and
b) an effective amount of a further medicament active ingredient.

The set comprises suitable containers, such as boxes, individual bottles, bags or ampoules. The set may comprise, for example, separate ampoules in each of which an effective amount of a compound of the formula I and/or pharmaceutical acceptable derivatives, solvates, stereoisomers thereof, including mixtures thereof in all ratios, and an effective amount of a further medicament active ingredient is present in dissolved or lyophilised form.

Suitable for enteral administration (oral or rectal) are, in particular, tablets, dragees, capsules, syrups, juices, drops or suppositories, suitable for parenteral administration (subcutaneous or intravenous) are solutions, preferably oily or aqueous solutions, furthermore suspensions, emulsions or implants, suitable for topical application are ointments, creams, pastes, lotions, gels, sprays, foams, aerosols, solutions (for example solutions in alcohols, such as ethanol or isopropanol, acetonitrile, DMF, dimethylacetamide, 1,2-propanediol or mixtures thereof with one another and/or with water) or powders. Liposomal compositions also come into consideration, in particular for topical applications.

The compounds and/or physiologically acceptable salts and solvates thereof may also be lyophilised and the resultant lyophilisates used, for example, for the preparation of injection preparations. They can furthermore be administered as nasal sprays.

The compounds according to the invention can be administered to humans or animals, in particular mammals, such as apes, dogs, cats, rats or mice, and used in the therapeutic treatment of the human or animal body and in combating the above-mentioned diseases. They can furthermore be used as diagnostic agents or as reagents.

On use of compositions or medicaments according to the invention, the compounds according to the invention and/or physiologically acceptable salts and solvates thereof are generally used analogously to known, commercially available compositions or preparations, preferably in doses between 0.1 and 500 mg, in particular 5 and 300 mg, per administration unit. The daily dose is preferably between 0.001 and 250 mg/kg, in particular 0.01 and 100 mg/kg, of body weight. The composition may be administered one or more times per day, for example twice, three times or four times per day. However, the individual dose for a patient depends on a large number of individual factors, such as, for example, on the efficacy of the compound used in each case, on the age, body weight, general state of health, sex, diet, on the time and method of administration, on the excretion rate, on the combination with other medicaments and on the severity and duration of the particular disease. Oral administration is preferred.

A measure of the uptake of a medicament active ingredient in an organism is its bioavailability. If the medicament active ingredient is supplied intravenously to the organism in the form of an injection solution, its absolute bioavailability, i.e. the fraction of the drug which reaches the systemic blood, i.e. the general circulation, in unchanged form, is 100%. In the case of oral administration of a therapeutic active ingredient, the active ingredient is generally in the form of a solid in the formulation and must therefore first be dissolved so that it is able to overcome the entry barriers, for example the gastrointestinal tract, the oral mucous membrane, nasal membranes or the skin, in particular the stratum corneum, or can be absorbed by the body. Pharmacokinetic data, i.e. on the bioavailability, can be obtained analogously to the method of J. Shaffer et al., J. Pharm. Sciences, 88 (1999), 313-318.

Even without further embodiments, it is assumed that a person skilled in the art will be able to utilise the above description in the broadest scope. The preferred embodiments should therefore merely be regarded as descriptive disclosure, but absolutely not as a disclosure which is limiting in any way. The following examples are intended to explain the invention without limiting it. Unless stated otherwise, percentages denote per cent by weight. All temperatures are indicated in degrees Celsius. "Conventional work-up": water is added if necessary, pH values of between 2 and 10 are set if necessary, depending on the constitution of the end product, the mixture is extracted with ethyl acetate or dichloromethane, the phases are separated, the organic phase is dried over sodium sulfate, filtered and evaporated, and the residue is purified by chromatography on silica gel and/or by crystallisation.

Rf values on silica gel;
Mass spectrometry: EI (electron impact ionisation): M$^+$
FAB (fast atom bombardment): (M+H)$^+$ THF (tetrahydrofuran), NMP (N-methylpyrrolidone), DMSO (dimethyl sulfoxide), EA (ethyl acetate), MeOH (methanol), TLC (thin-layer chromatography)

The following substances have been synthesised and characterised. However, the substances can also be prepared and characterised by the person skilled in the art by other methods.

EXAMPLE 1

Synthesis of 5-{4-[4-(5-cyano-2-oxo-2,3-dihydro-1H-indol-3-yl)butyl]-piperazin-1-yl}benzofuran-2-carboxamide

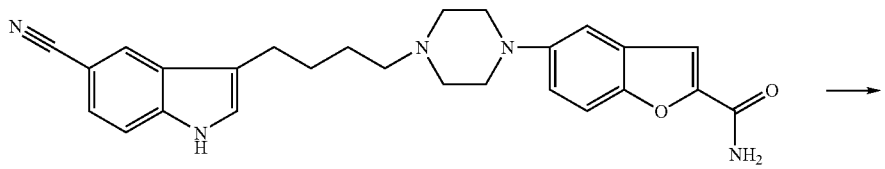

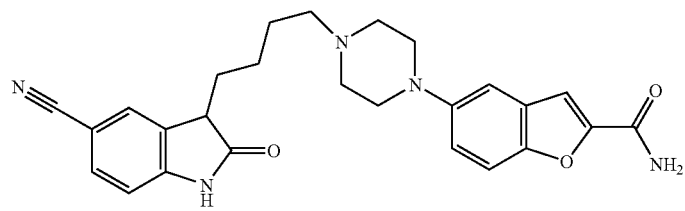

4.78 g (10 mmol) of 5-{4-[4-(5-cyano-3-indolyl)butyl]-1-piperazinyl}benzo-furan-2-carboxamide are dissolved in 28.4 ml of hot DMSO. After cooling to room temperature, 66.4 ml of conc. HCl are added dropwise with stirring. The batch temperature is held at 24° C. by cooling by means of an ice bath. When the addition of HCl is complete, the batch is stirred at room temperature for 10 h. The crystal slurry is subsequently stirred with 50 ml of acetone, filtered off with suction and rinsed with acetone, isopropanol and diethyl ether. The resultant crystals were dried in air.

m.p.: 238° C. (decomp.)

In the following thin-layer systems, associated RF values are determined:
$CH_2Cl_2$/MeOH/EA (7:2:1)=0.32;
EA/MeOH (8:2)=0.18
Sought C, 56.9%; H, 5.7%; Cl, 13.9%; N, 12.8%.
Found C, 56.2%; H, 5.6%; Cl, 13.1%; N, 12.8%.
calculated on the basis of 2×HCl with 1×$H_2O$.

EXAMPLE 2

Synthesis of 5-{4-[4-(5-fluoro-2-oxo-2,3-dihydro-1H-indol-3-yl)butyl]-piperazin-1-yl}benzofuran-2-carboxamide

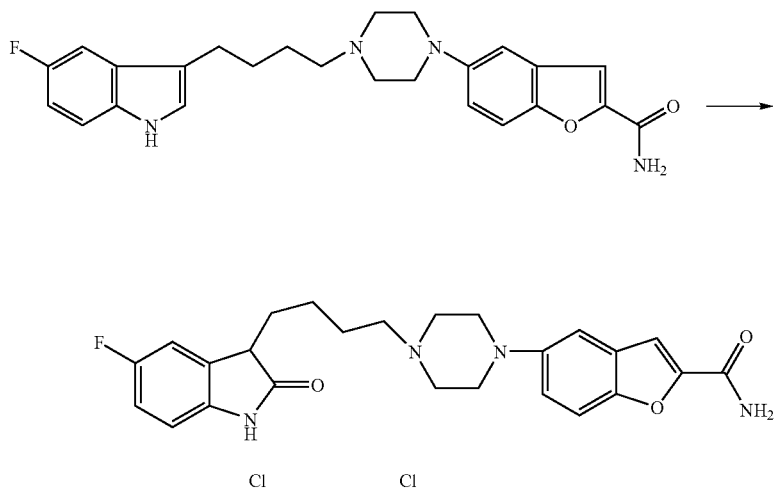

0.5 g of 5-{4-[4-(5-fluoro-1H-indol-3-yl)butyl]piperazin-1-yl}benzofuran-2-carboxamide are dissolved in 2.8 ml of DMSO, and 5.4 ml of conc. HCl are added with stirring. The temperature is held at a max. of 35° C. using a coldwater bath, and precipitate formation occurs during stirring. The suspension is stirred into 150 ml of acetone, the crystals are filtered off with suction, rinsed with acetone and dried in air, giving 0.5 g of grey crystals having a melting point of 249-252° C.
calculated C=56.3% H=5.6% Cl=13.3% N=10.5%
found C=55.9% H=5.5% Cl=14.3% N=10.5%
calculated on the basis of 2×HCl.

EXAMPLE 3

Synthesis of 5-{4-[4-(5-cyano-6-hydroxy-1H-indol-3-yl)butyl]piperazin-1-yl}-benzofuran-2-carboxamide

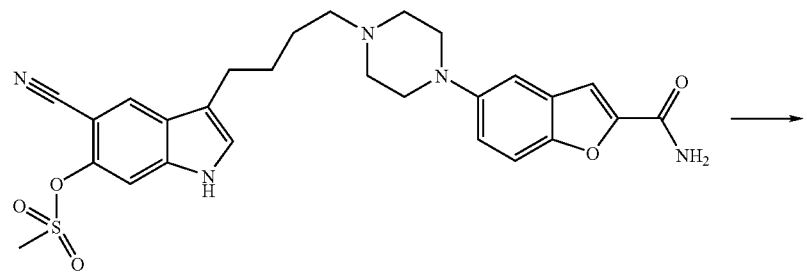

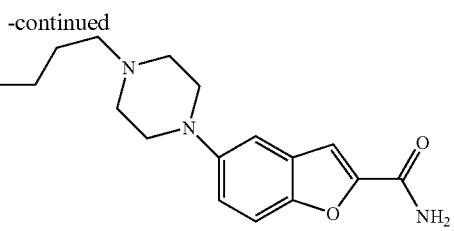

260 mg (0.4 mmol) of the dihydrochloride of 3-{4-[4-(2-carbamoylbenzo-furan-5-yl)piperazin-1-yl]butyl}-5-cyano-1H-indol-6-yl methanesulfonate and 5 g (89 mmol) of potassium hydroxide pellets are stirred for 48 h at room temperature in 75 ml of methanol. The solution is subsequently adjusted to a pH of 3 using 1N HCl and evaporated to dryness. The residue is purified by thick-layer chromatography using methanol as solvent.

The crystals isolated from the support material are dissolved in acetone, and 1N HCl is added until a pH of 2 has been set. The cloudy solution is evaporated to dryness, stirred with ether and filtered with suction.

The compound is isolated as the hydrochloride [M+H$^+$] HPLC/MS=458.

EXAMPLE 4

Synthesis of 5-{4-[4-(5-cyano-2,3-dihydro-1H-indol-3-yl)butyl]piperazin-1-yl}benzofuran-2-carboxamide a) Synthesis of 3-(4-chlorobutyl)-2,3-dihydro-1H-indole-5-carbonitriles

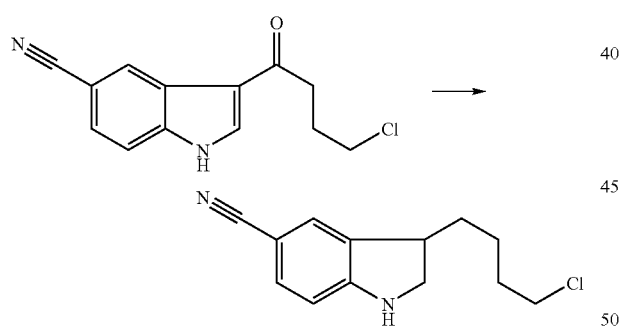

5 g (20 mmol) of 3-(4-chlorobutyryl)-1H-indole-5-carbonitrile in 70 ml of trifluoroacetic acid are initially introduced, and 5.9 g (51 mmol) of triethylsilane are added dropwise at room temperature. The mixture is stirred at room temperature for a further 72 h, during which a clear solution is not formed. The reaction mixture is subsequently poured into ice-water, rendered alkaline using sodium hydroxide and extracted to exhaustion with ethyl acetate. The combined organic phases are dried over sodium sulfate and evaporated to dryness in a rotary evaporator. The residue is fractionated by chromatography over silica gel using dichloromethane, giving a pale oil which exhibits an Rf value of 0.3 in the toluene/methanol/triethylamine=7:2:1 TLC system.

b) Synthesis of 5-{4-[4-(5-cyano-2,3-dihydro-1H-indol-3-yl)butyl]piperazin-1-yl}benzofuran-2-carboxamide

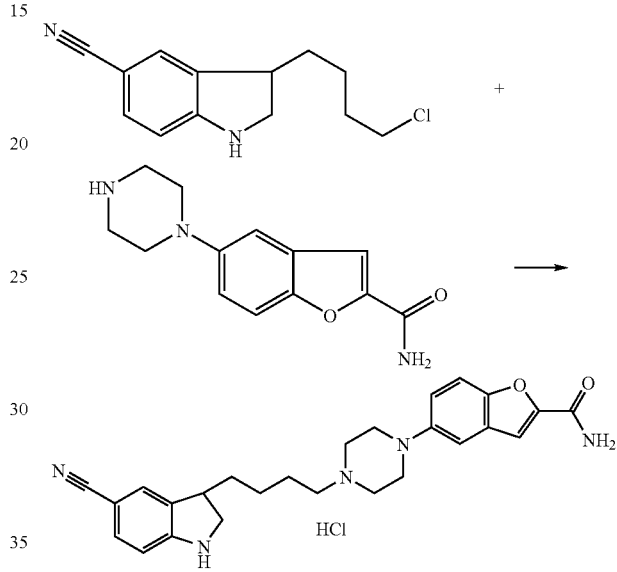

2.5 g (11 mmol) of the halide prepared as described in a) are dissolved in 50 ml of NMP, and 2.6 g (11 mmol) of 5-piperazin-1-ylbenzofuran-2-carboxamide are added with stirring. The batch is stirred at 125° C. for 24 h. For work-up, the suspension is stirred into 500 ml of ice-water, adjusted to pH 10 using 4% sodium hydroxide solution and extracted three times with 100 ml of ethyl acetate each time. The combined organic phases are washed twice with 100 ml of water each time, dried over sodium sulfate, filtered and evaporated to dryness, giving 2.3 g of crude substance. The residue is chromatographed over silica gel using ethyl acetate and methanol (ratio=9:1), giving 1.5 g of purified product, which is dissolved in 150 ml of acetone and precipitated as pale-brown hydrochloride using one molar hydrochloric acid (pH 3).

The substance has a retention of 0.7 in the methanol/triethylamine=8:2 thin-layer system and melts between 166.5-168.0° C. Elemental analysis (%): calculated for hydrochloride hydrate C, 62.69; H, 6.49; Cl, 7.12; N, 14.06 found C, 61.9; H, 6.5; Cl, 6.9; N, 13.6.

EXAMPLE 5

Results of the Receptor Binding Tests

Many of the compounds synthesised have nanomolar affinity to the 5-HT$_{1A}$ receptors and nanomolar reuptake inhibition of serotonin.

5-{4-[4-(5-Cyano-2-oxo-2,3-dihydro-1H-indol-3-yl)butyl]piperazin-1-yl}-benzofuran-2-carboxamide

| 5 HT$_{1A}$ | 1.7 nmol/l (IC50) |
|---|---|
| SSRI | 2.9 nmol/l (IC50) |

5-{4-[4-(5-Cyano-6-hydroxy-1H-indol-3-yl)butyl]piperazin-1-yl}benzofuran-2-carboxamide

| 5 HT$_{1A}$ | 18 nmol/l (IC50) |
|---|---|
| SSRI | 2.7 nmol/l (IC50) |

EXAMPLE 6

Injection Vials

A solution of 100 g of a compound of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of a compound of the formula I.

EXAMPLE 7

Suppositories

A mixture of 20 g of a compound of the formula I is melted with 100 g of soya lecithin and 1400 g of cocoa butter, poured into moulds and allowed to cool. Each suppository contains 20 mg of a compound of the formula I.

EXAMPLE 8

Solution

A solution is prepared from 1 g of a compound of the formula I, 9.38 g of NaH$_2$PO$_4$2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE 9

Ointment 500 mg of a compound of the formula I are mixed with 99.5 g of Vaseline under aseptic conditions.

EXAMPLE 10

Tablets

A mixture of 1 kg of a compound of the formula I, 4 kg of lactose, 1.2 kg of potato starch, 0.2 kg of talc and 0.1 kg of magnesium stearate is pressed in a conventional manner to give tablets in such a way that each tablet contains 10 mg of a compound of the formula I.

EXAMPLE 11

Dragees

Tablets are pressed analogously to Example E and subsequently coated in a conventional manner with a coating of sucrose, potato starch, talc, tragacanth and dye.

EXAMPLE 12

Capsules 2 kg of a compound of the formula I are introduced in a conventional manner into hard gelatine capsules in such a way that each capsule contains 20 mg of a compound of the formula I.

EXAMPLE 13

Ampoules

A solution of 1 kg of a compound of the formula I in 60 l of bidistilled water is sterile filtered, transferred into ampoules, lyophilised under sterile conditions and sealed under sterile conditions. Each ampoule contains 10 mg of a compound of the formula I.

The invention claimed is:
1. Compounds of the formula I

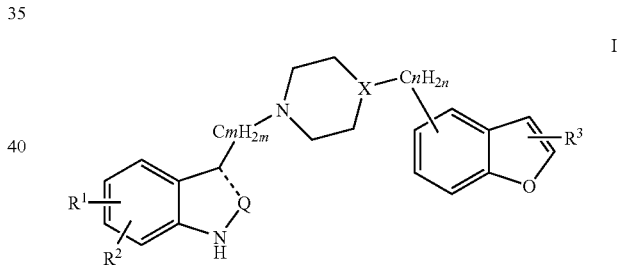

in which
X=N or CH,
R$^1$, R$^2$, R$^3$=independently of one another OH, OA, CN, Hal, COR$^4$ or CH$_2$R$^4$,
R$^4$=OH, OA, NH$_2$, NHB or NB$_2$,
Q=CH$_2$ or CO,
A, B=independently of one another straight-chain or branched alkyl or alkoxy having 1 to 10 C atoms, alkenyl having 2 to 10 C atoms or alkoxyalkyl having 2 to 10 C atoms,
m=2, 3, 4, 5 or 6 and
n=0, 1, 2, 3 or 4,
or physiologically acceptable salts or stereoisomers thereof, including mixtures thereof in all ratios.
2. Compounds according to claim 1 in which
X=N,
R$^1$, R$^2$, R$^3$=independently of one another CN, OH, COR$^4$ or CH$_2$R$^4$,
R$^4$=OH, NH$_2$, NHB or NHB$_2$,
Q=CH$_2$ or CO, B=alkyl having 1-6 C atoms,
m=4 and
n=0,
or physiologically acceptable salts or stereoisomers thereof, including mixtures thereof in all ratios.

3. A compound of the formula
a) 5-{4-[4-(5-cyano-2,3-dihydro-1H-indol-3-yl)butyl]piperazin-1-yl}benzo-furan-2-carboxamide

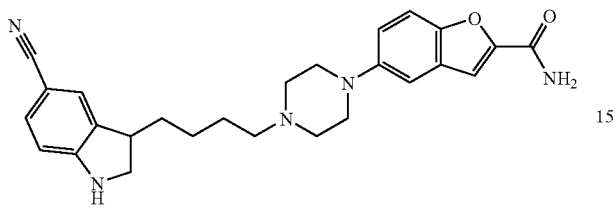

b) 5-{4-[4-(5-cyano-2-oxo-2,3-dihydro-1H-indol-3-yl)butyl]piperazin-1-yl}-benzofuran-2-carboxamide

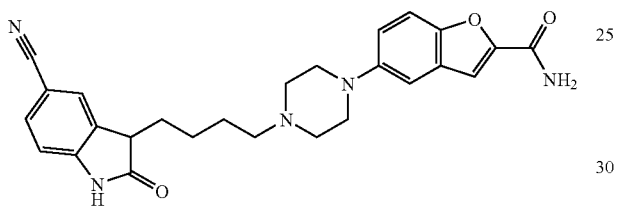

or
c) 5-{4-(5-fluoro-2-oxo-2,3-dihydro-1H-indol-3-yl)butyl]piperazin-1-yl)-benzofuran-2-carboxamide or

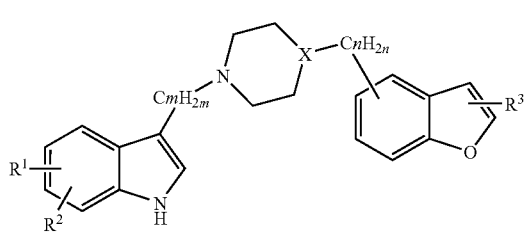

4. Process for the preparation of compounds according to claim 1 or physiologically acceptable salts or stereoisomers thereof, comprising
a) reacting a compound of the formula II, in which $R^1$, $R^2$, $R^3$, X, m and n have the meanings indicated in claim 1,

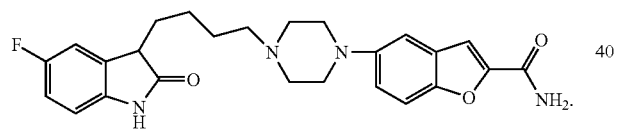

with dimethyl sulfoxide and concentrated HCl, or
b) reacting a compound of the formula III, in which $R^1$, $R^2$, and n have the meanings indicated in claim 1, and Y is a halogen or an alcohol provided with protecting groups,

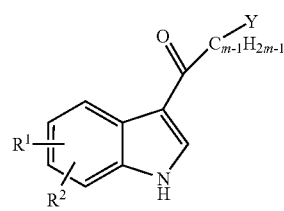

with trifluoroacetic acid and triethylsilane and subsequently coupling with a compound of the formula IV, in which $R^3$, X and n have the meanings indicated in claim 1

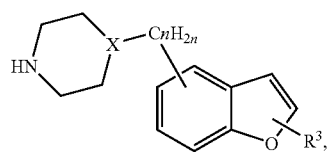

and reacting with dimethyl sulfoxide and concentrated HCl or
c) reacting a compound of the formula V, in which $R^2$ and m have the meanings indicated in claim 1 and Y is a halogen, or an alcohol provided with protecting groups,

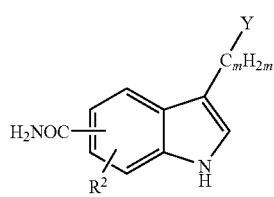

with a dehydrating reagent and subsequently coupling with a compound of the formula IV, and reacting with dimethyl sulfoxide and concentrated HCl.

5. Pharmaceutical composition comprising at least one compound according to claim 1 and/or physiologically acceptable salts or stereoisomers thereof, including mixtures thereof in all ratios, and a pharmaceutically acceptable carrier.

6. Pharmaceutical composition, according to claim 5 comprising further excipients and/or adjuvants.

7. Process for the preparation of a pharmaceutical composition, comprising bringing a compound according to claim 1 and/or one of its physiologically acceptable salts or stereoisomers, including mixtures thereof in all ratios, into a suitable dosage form together with a solid, liquid or semi-liquid excipient or adjuvant.

8. A method of achieving an anxiolytic, antidepressant, neuroleptic and/or antihypertonic effect and for treating migraine or obsessive compulsive disorder, comprising administering to a host in need thereof an effective amount of a compound according to claim 1 and/or physiologically acceptable salts or stereoisomers thereof, including mixtures thereof in all ratios.

* * * * *